United States Patent [19]

Shealy et al.

[11] Patent Number: 4,728,736

[45] Date of Patent: Mar. 1, 1988

[54] CARBOCYCLIC ANALOGS OF PURINE RIBOFURANOSIDES

[75] Inventors: Y. Fulmer Shealy, Birmingham; Joe D. Clayton, Brookside, both of Ala.

[73] Assignee: Southern Research Institute, Birmingham, Ala.

[21] Appl. No.: 594,372

[22] Filed: Mar. 28, 1984

[51] Int. Cl.$^4$ ............................................. C07D 239/00
[52] U.S. Cl. ....................................... 544/254; 536/24; 536/26; 544/264; 544/265; 544/267; 544/277
[58] Field of Search ................... 424/180, 253; 536/24, 536/26; 544/264, 265, 277, 267, 259

[56] References Cited

U.S. PATENT DOCUMENTS

| 4,138,562 | 2/1979 | Vince | 544/326 |
| 4,268,672 | 5/1981 | Vince | 544/265 |
| 4,383,114 | 5/1983 | Vince | 544/277 |

OTHER PUBLICATIONS

Journal of Pharmaceutical Sciences, vol. 62, pp. 1432-1434, 1973 ©, Y. F. Shealy and J. D. Clayton.
Journal of Pharmaceutical Sciences, vol. 69, pp. 1019-1021, 1980, H. Lee and R. Vince.
Shealy et al., Carbocyclic Analogs of Guanosine and 8-Azaguanosine, J. Pharm. Sciences, 62, 1432 (1973 ©).
Lee et al., Carbocyclic Analogs of Arabinosylpurine Nucleosides, J. Pharm. Sciences, 69, 1019 (1980).
Shealy et al., Carbocyclic Analog of Purine Ribonucleosides with Antileukemic Activity, Chem. Abstracts, 79:100484k (1973a).
Shealy et al., Carbocyclic Analogs of 6-Substituted Purine Ribonucleosides and of Adenosine Ribonucleotides, Chem. Abstracts, 79:92531f (1973b).
Vince et al., Carbocyclic Arabinosyladenine..., Chem. Abstracts, 86:165109f (1977).

*Primary Examiner*—J. R. Brown
*Assistant Examiner*—L. Eric Crane
*Attorney, Agent, or Firm*—Roylance, Abrams, Berdo & Goodman

[57] ABSTRACT

There are disclosed carbocyclic analogs of 2-amino-6-substituted-purine ribofuranosides and 2-amino-6-substituted-8-azapurine ribofuranosides. These compounds are useful in the treatment of viral infections.

8 Claims, No Drawings

CARBOCYCLIC ANALOGS OF PURINE RIBOFURANOSIDES

BACKGROUND OF THE INVENTION

This invention relates to carbocyclic analogs of 2-amino-6-substituted-purine ribofuranosides and 2-amino-6-substituted-8-azapurine ribofuranosides. This invention also relates to the use of such compounds in the treatment of viral infections.

The term "carbocyclic analog of a nucleoside" designates a compound that has the same chemical structure as the nucleoside except that the oxygen atom of the furanose moiety of the nucleoside is replaced by a methylene group in the carbocyclic analog; or, differently expressed, in the carbocyclic analog a cyclopentane ring replaces the tetrahydrofuran ring of the analogous nucleoside. Such nucleoside analogs were designated carbocyclic analogs of nucleosides by Shealy and Clayton, *Journal of the American Chemical Society*, Volume 88, pages 3885–3887, 1966. The natural nucleosides and many of their true nucleoside analogs are subject to the action of enzymes (phosphorylases and hydrolases) that cleave the nucleosides to the pentose and purine or pyrimidine moieties. The biological effects of such true nucleoside analogs may be lessened by the action of these degradative enzymes. In contrast, carbocyclic analogs of nucleosides do not possess the glycosidic bond present in the true nucleosides and, therefore, are not subject to the action of these degradative enzymes. They may also be more selective in their biological actions.

The synthesis of the carbocyclic analog of guanosine (Formula II with Y=O) was reported earlier by Y. F. Shealy and J. D. Clayton in the *Journal of Pharmaceutical Sciences*, Volume 62, pages 1432–1434, 1973. The carbocyclic analog of guanosine is a carbocyclic analog of a ribofuranoside of a 2-amino-6-substituted-purine. The carbocyclic analogs of 8-azaguanosine (Formula IV with Y=O) and of 2-amino-6-chloro-8-azapurine ribofuranoside (Formula III with X=Cl) were reported in the same article in the *Journal of Pharmaceutical Sciences*. These two compounds are carbocyclic analogs of ribofuranosides of 2-amino-6-substituted-8-azapurines. The preparation in situ and the use of the carbocyclic analog (Formula I with X=Cl; Example 1) of 2-amino-6-chloropurine ribofuranoside as an intermediate were reported by Shealy and Clayton (loc. cit.), but the preparation of a pure specimen has not been reported. The carbocyclic analogs of three arabinofuranosides of 2-amino-6-substituted-purines and of three arabinofuranosides of 2-amino-6-substituted-8-azapurines were reported by H. Lee and R. Vince (*Journal of Pharmaceutical Sciences*, Volume 69, pages 1019–1021, 1980). These arabinofuranoside analogs either were not active against type 1 herpes simplex virus or were much less active than are the corresponding ribofuranoside analogs of this invention. The compounds of this invention differ in structure from the arabinofuranoside analogs of Lee and Vince. In the ribofuranoside analogs of this invention, the two secondary hydroxyl groups attached to the cyclopentane ring are cis to each other, whereas they are trans to each other in the arabinofuranosides.

SUMMARY OF THE INVENTION

It has now been found that certain carbocyclic analogs of 2-amino-6-substituted-purine ribofuranosides and of 2-amino-6-substituted-8-azapurine ribofuranosides are highly active in inhibiting the replication of herpes viruses. Thus, in accordance with this invention, there is administered to a host animal, including man, afflicted with a viral infection a therapeutically effective amount of a carbocyclic analog of a nucleoside represented by one of the following formulas:

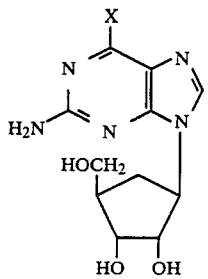

Formula I

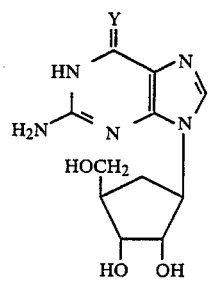

Formula II

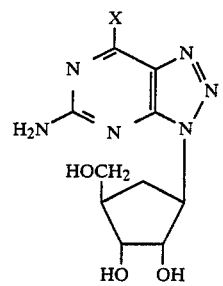

Formula III

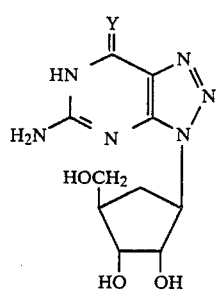

Formula IV wherein X is a halogen, an amino group, an alkylamino group, preferably a lower alkylamino group, an alkoxy group, preferably a lower alkoxy group, or an alkylthio group, preferably a lower akylthio group and Y is oxygen or sulfur. By "lower" is meant a group containing from 1 to 6 carbon atoms.

Also, in accordance with this invention, there are provided novel compounds as defined by formulas I, II, III and IV wherein X is fluorine, iodine or bromine, an amino group, an alkylamino group, preferably a lower alkylamino group, an alkoxy group, preferably a lower alkoxy group, or an akylthio group, preferably a lower akylthio group and Y is sulfur.

DETAILED DESCRIPTION OF THE INVENTION

Pyrimidines represented by Formula V are precursors of the carbocyclic analogs of Formulas I, II, III and IV;

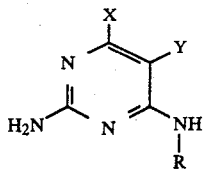

Formula V wherein R=R' or a derivative thereof and R'=

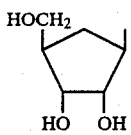

The synthesis of precursor V with X=Cl, Y=NH$_2$, and R=R' was described in the article by Shealy and Clayton (loc. cit.). Compounds of Formulas I and II may be prepared by converting this pyrimidine V to the 2-amino-6-chloropurine (Formula I with X=Cl) by treating it with a reagent, such as triethyl orthoformate, that forms a purine from a 4,5-diaminopyrimidine. The 2-amino-6-chloropurine (Formula I with X=Cl; Example 1) has not been isolated previously in pure form. Other carbocyclic analogs (Formulas I and II) of ribofuranosides of 2-amino-6-substituted-purines may be prepared by treating the 2-amino-6-chloropurine with an appropriate nucleophilic reagent; for example, treatment of the 2-amino-6-chloropurine derivative with ammonia produces the carbocyclic analog (Formula I with X=NH$_2$; Example 2) of 2,6-diaminopurine riboside, and treatment of the same 2-amino-6-chloropurine with a thiolating agent yields the carbocyclic analog (Formula II with Y=S; Example 5) of thioguanosine. The 8-azapurine derivatives (Formulas III and IV) are prepared similarly except that pyrimidine V with X=Cl, Y=NH$_2$, and R=R' is treated with a nitrosating agent to form the carbocyclic analog (Formula III with X=Cl) of 2-amino-6-chloro-8-azapurine ribofuranoside. Treatment of this 2-amino-6-chloro-8-azapurine derivative with nucleophilic reagents yields 8-azapurines (1,2,3-triazolo[4,5-d]pyrimidines) represented by Formulas III and IV; e.g., Examples 6 and 7.

The carbocyclic analogs of 2-amino-6-substituted-purine nucleosides and of 2-amino-6-substituted-azapurine nucleosides of this invention inhibit the replication of DNA viruses. Certain representatives of Formulas I-IV have potent antiviral activity and may be useful for the treatment of virus-induced diseases. The antiviral activity of compounds represented by Formulas I-IV was measured as a virus rating (VR), and the potency (MIC$_{50}$) was determined as the concentration of the tested compound required to inhibit virus-induced cytopathogenic effects in host cells by 50%. The carbocyclic analog (Example 2) of 2,6-diaminopurine riboside displayed high activity (VR=4.6) and potency (MIC$_{50}$=0.32 mcg./ml.) in a test against herpes simplex virus, type 1, replicating in human epidermoid carcinoma cells. In this test and during tests of other ribofuranoside analogs (Formulas I-IV), 1-$\beta$-D-arabinofuranosyladenine (ara-A), an antiviral drug employed in medical practice, was used as a positive control in these tests and was found to be less active (VR=2.0-2.2) and less potent (MIC$_{50}$=2.5-10 mcg./ml.) than was the carbocyclic analog of Example 2. The ribofuranoside analog of Example 2 is also highly active in inhibiting replication of vaccinia virus, and certain other ribofuranoside analogs have significant activity against herpes simplex and vaccinia viruses as illustrated by the results summarized in Example 9.

The compounds of this invention are illustrated by, but are not limited to, the following examples. The system of designating the orientation of substituents on the cyclopentane ring as $\alpha$ or $\beta$ is that used by *Chemical Abstracts*, beginning with Volume 76, in the Chemical Substance Index. In the examples illustrating syntheses of the compounds of this invention, data were acquired and are reported as follows. Decomposition and melting temperatures (m.p.) were determined in capillary tubes. Ultraviolet spectra (UV) were recorded with a recording spectrophotometer and absorption maxima are reported in nanometers; sh=shoulder. Solutions for ultraviolet spectral determinations were prepared by diluting a 5-ml. aliquot of a water solution to 50 ml. with 0.1N hydrochloric acid, phosphate buffer (pH 7), or 0.1N sodium hydroxide. Absorption maxima of these solutions are reported as being determined at pH 1, 7, or 13, respectively. Infrared spectra (IR) were recorded from samples in pressed potassium bromide discs; s=strong, vs=very strong, sh=shoulder, w=weak. Mass spectral data (MS) were taken from low-resolution, electron-impact spectra determined at 70 eV. The peaks listed are those arising from the molecular ion (M), those attributable to the loss of certain fragments (M minus a fragment), and some other prominent peaks. Fragments containing the complete purine or pyrimidine moiety may be designated P plus an atom or group. Nuclear magnetic resonance spectra were determined at 100 MHz for proton ($^1$H NMR) spectra. The internal standard was tetramethylsilane; s=singlet, t=triplet, m=multiplet. Thin-layer chromatography (TLC) was performed on plates of silica gel, and developed plates were examined by ultraviolet light.

EXAMPLE 1

(1$\alpha$,2$\alpha$,3$\beta$,5$\beta$)-3-(2-Amino-6-chloro-9HH-purin-9-yl)-5-(hydroxymethyl)-1,2-cyclopentanediol (Formula I, X=Cl)

To a mixture of 1.45 g. of pyrimidine V (with X=Cl, Y=NH$_2$, and R=R'), 15 ml. of dimethylacetamide, and 10 ml. of triethyl orthoformate at 0°-5° C. was added 0.5 ml. of 12N hydrochloric acid. The mixture was stirred at room temperature for 20 hours, during which time it became homogeneous. The solution was concentrated under reduced pressure (oil pump) to a red syrup, which was concentrated further by adding and evaporating toluene in vacuo. A solution of the syrup in 60 ml. of 50% acetic acid was stirred at room temperature for 4 hours and then concentrated in vacuo to a dark red syrup. A solution of this syrup in 50 ml. of ammonia-methanol (8% NH$_3$) was stirred at room temperature for 4 hours and concentrated in vacuo. Several portions of methanol were added to and evaporated from the residue. A methanol solution of the crude product was diluted with water (15 ml.) and concentrated in vacuo to remove most of the methanol. The aqueous solution was diluted with acetonitrile (5 ml.), seeded with previously obtained crystals of the compound of Example 1, and stored in a refrigerator. The red crystalline precipitate was collected by filtration, washed with acetonitrile-water (1:1), and dried in vacuo over $P_2O_5$: yield, 770 mg. (52%); m.p. 206°–210° C. dec. A second crop (100 mg., 7%) of crude product was obtained by diluting the filtrate with acetonitrile and chilling the mixture to −20° C. The two crops were combined, and the crude product was recrystallized from water (10 ml.): yield, 633 mg. (43%); m.p. 216°–218° C. dec. This material was suitable for the preparation of other 2-amino-6-substituted-purines. A specimen was recrystallized from water: m.p., 222°–224° C. dec. (inserted at 210° C., 2°/min.); UVmax 313 nm (ε7000), 242 (ε5500), 221 (ε25,100) at pH 1; 307 (ε7600), 245 (ε5100, 223 (ε27,000) at pH 7; MS (direct-probe temperature, 20° C.), m/e 299 (M), 282 (M−OH), 268 (M−CH$_2$OH), 252 (M−OH−CH$_2$OH+H), 250 (M−H$_2$O−CH$_2$OH), 225, 224 (M−75), 196 (P+C$_2$H$_4$), 170 (P+2H), 169 (P+H); $^1$H NMR (Me$_2$SO-d$_6$) δ1.4–2.4 (m, C$\underline{H}_2$ and CH—CH$_2$OH), 3.49 (m, CH$_2$OH), 3.84 (m, —CHOH—CH—CH$_2$OH), 4.28 (m, —N—CH—C$\underline{H}$OH), 4.62 (m, —N—C$\underline{H}$—), ca. 3.4–5.2 (3 OH), 6.82 (s, NH$_2$), 8.25 (s, purine C$\underline{H}$).

Analysis. Calcd. for $C_{11}H_{14}ClN_5O_3$: C, 43.55; H, 4.72; N, 23.07. Found: C, 43.51; H, 4.51; N, 22.97.

EXAMPLE 2

(1α,2α,3β,5β)-3-(2,6-Diamino-9H-purin-9-yl)-5-(hydroxymethyl)-1,2-cyclopentanediol (The Carbocyclic Analog of 2,6-Diaminopurine Ribofuranoside; Formula I, X=NH$_2$)

A solution of 500 mg. of the 2-amino-6-chloropurine of Example 1 in 50 ml. of liquid ammonia was heated for 20 hours at 80° C. in a stainless steel bomb containing a glass liner. After the bomb had been chilled and opened, the ammonia was evaporated with a current of nitrogen, and water was twice added to and evaporated from the residue. The product was converted to the sulfate salt by dissolving the residue in water (about 3 ml.) and diluting the solution with 1.8M sulfuric acid (2.3 ml.) and then with ethanol (6 ml.). A precipitate was collected by filtration, washed with 50% ethanol, and dried in vacuo at 78° C.; weight, 516 mg. The crude sulfate was recrystallized from 50% ethanol (30 ml.) containing two drops of 1.8M sulfuric acid and was dried at 78° C. over $P_2O_5$: yield, 487 mg. [84% as a sulfate hydrate (0.5H$_2$SO$_4$.H$_2$O)]; m.p., 245°–248° C. dec. (inserted at 195° C.); IR (1700–1500 cm$^{-1}$ region) 1695 s, 1655 s, 1625, 1570, 1530; MS (direct-probe temperature, 130° C.), m/e 280 (M), 263 (M−OH), 249 (M−CH$_2$OH), 233 (M−OH−CH$_2$OH+H), 231 (M−H$_2$O−CH$_2$OH), 205 (M−75), 177 (P+C$_2$H$_4$), 151 (P+2H), 150 (P+H); UVmax 291 nm (ε10,400), 253 (ε10,200) 218 (ε22,400) at pH 1; 280 (ε10,700), 256 (ε8700), 250 sh, 216 (ε29,200) at pH 7; 281 (ε10,900), 256 (ε8700), 250 sh at pH 13; $^1$H NMR (Me$_2$SO-d$_6$) δ1.4–2.4 (m, C$\underline{H}_2$ and CHCH$_2$OH), 3.48 (m, C$\underline{H}_2$OH), 3.84 (m, —CHOH—CH—CH$_2$OH), 4.24 (m, —N—CH—C$\underline{H}$OH), 4.60 (m, —N—C$\underline{H}$), 5.14 (m, broad, OH, H$_2$O, NH$_3$), 7.8 (NH$_2$), 8.04 (s, purine CH).

Analysis. Calcd. for $C_{11}H_{16}N_6O_3.0.5H_2SO_4.H_2O$: C, 38.04; H, 5.51; N, 24.20. Found: C, 37.85; H, 5.30; N, 24.20.

EXAMPLE 3

(1α,2α,3β,5β)-3-[2-Amino-6-(methylamino)-9H-purin-9-yl]-5-(hydroxymethyl)-1,2-cyclopentanediol (Formula I, X=NHCH$_3$)

The 2-amino-6-chloropurine of Example 1 (200 mg.) was treated with methylamine (25 ml.) by the method described for the preparation of the compound of Example 2. The reaction mixture from the bomb was concentrated to dryness, and the residue was dissolved in a mixture of water (3 ml.), ethanol (3 ml.), and 1.8M sulfuric acid (1 ml.). The solution was filtered and concentrated under reduced pressure by adding several portions of ethanol during the concentration. A hot solution of the residual thin syrup in ethanol (10 ml.) was filtered, and the filtrate was re-warmed to dissolve a slight precipitate, allowed to stand at room temperature, and then stored in a refrigerator overnight. The white crystalline sulfate was collected by filtration, dried in vacuo at room temperature over $P_2O_5$, and recrystallized from 80% ethanol (5 ml.). The white solid was dried in vacuo over $P_2O_5$ at 78° C. for 4 hours: yield, 172 mg. (69% as the sulfate 1.5 hydrate); m.p. 166°–168° C. dec.; MS (direct-probe temperature, 150° C.), m/e 294 (M), 277 (M−OH), 263 (M−CH$_2$OH), 247 (M−OH−CH$_2$OH+H), 245 (M−H$_2$O−CH$_2$OH), 219 (M−75), 191 (P+C$_2$H$_4$), 165 (P+2H), 164 (P+H); UVmax 291 nm (ε11,500), 255 (ε10,400), 216 sh, 208 (ε19,200) at pH 1; 281 (ε13,600), 262 sh, 215 (ε23,800) at pH 7; 281 (ε13,600), 262 sh at pH 13.

Analysis. Calcd. for $C_{12}H_{18}N_6O_3.0.5H_2SO_4.1.5H_2O$: C, 38.92; H, 5.99; N, 22.69. Found: C, 39.19; H, 5.60; N, 23.02.

EXAMPLE 4

(1α,2α,3β,5β)-3-[2-Amino-6-(methylthio)-9H-purin-9-yl]-5-(hydroxymethyl)-1,2-cyclopentanediol (Formula I, X=—SCH$_3$)

A mixture of 300 mg. of the 2-amino-6-chloropurine of Example 1, 10 ml. of methanol (dried over molecular sieves), and 2 ml. of 1.0N sodium methoxide was cooled to 5° C. and saturated with methanethiol. The solution was heated at 104° C. for 18 hours in a stainless steel bomb containing a glass liner. After the bomb had been chilled and opened, the reaction mixture was concentrated to dryness in vacuo, methanol (50 ml.) was added to and evaporated from the residue, and a solution of the residue in water (10 ml.) was neutralized to pH 7 with 1N hydrochloric acid. The neutral solution was concentrated to dryness in vacuo at 35° C., several portions of ethanol were added to and evaporated from the residue, and the residue was then leached with several portions of acetonitrile-ethanol (4:1). The extracts were combined, filtered, and concentrated to dryness in vacuo. A solution of the residue in water-acetonitrile (1:5) was concentrated to a glass that was homogeneous by TLC; weight, 248 mg.; MS, m/e 311 (M); Anal. for $C_{12}H_{17}N_5O_3S.H_2O$: C, 43.51; H, 5.72; N, 21.21. A solution of the glass in hot ethyl acetate to which a small amount of ethanol had been added deposited a white solid; two additional crops of solid were obtained by diluting the filtrate with hexane. The solid (three portions combined) was crystallized from ethanol-ethyl acetate, washed with ethyl acetate, and dried in vacuo over $P_2O_5$ at 78° C. for 2 hours: yield, 137 mg. (38% as an ethanolate); m.p. 105°–109° C. dec.; MS (direct-probe temperature, 80° C.) m/e 311 (M), 293

(M−H$_2$O), 280 (M−CH$_2$OH), 264 (M−OH−CH$_2$OH+H), 262 (M−H$_2$O−CH$_2$OH), 236 (M−75), 208 (P+C$_2$H$_4$), 182 (P+2H), 181 (P+H), 46 (EtOH); IR (1700–1500 cm$^{-1}$ region) 1620 s, 1580 s, 1565 s, 1500; UVmax 324 nm ($\epsilon$11,700), 261 sh, 248 ($\epsilon$9900), 227 ($\epsilon$16,600) at pH 1; 310 ($\epsilon$12,800), 245 ($\epsilon$12,100) 224 ($\epsilon$21,500) at pH 7; 310 ($\epsilon$12,900), 245 ($\epsilon$12,000), 224 ($\epsilon$20,900), a pH 13 (also, slight sh at 261 and 253 nm at pH 7 and 13); $^1$H NMR (Me$_2$SO-d$_6$) $\delta$1.06 (t, CH$_3$ of EtOH), 1.4–2.4 (m, CH$_2$ and CHCH$_2$OH), 2.58 (s, SCH$_3$), 3.48 (m, CH$_2$OH), 3.4 (CH$_2$ of EtOH, overlapped by the multiplet of the hydroxymethyl group), 3.84 (m, —CHOH—CH—CH$_2$OH), 4.26 (m, —N—CH—CHOH), 4.64 (m, —N—CH—), ca. 4.4–5.0 (OH), 6.4 (NH$_2$), 8.04 (s, purine CH).

Analysis. Calcd. for C$_{12}$H$_{17}$N$_5$O$_3$S·C$_2$H$_5$OH: C, 47.04; H, 6.49; N, 19.59. Found: C, 47.01; H, 6.42; N, 19.43.

EXAMPLE 5

2-Amino-1,9-dihydro-9-[(1α,2β,3β,4α)-2,3-dihydroxy-4-(hydroxymethyl)cyclopentyl]-6H-purine-6-thione (The Carbocyclic Analog of Thioguanosine; Formula II, Y=S)

A mixture of 150 mg. of the 2-amino-6-chloropurine of Example 1, 39 mg. of thiourea, and 5 ml. of 1-propanol was boiled under reflux for 2 hours, and the reaction mixture was chilled (−20° C.) and filtered to collect a yellow solid. The product was converted to the sulfate salt by dissolving the yellow solid (104 mg.) in hot water (1 ml.) and diluting the solution with 6M sulfuric acid (0.26 ml.) and then with ethanol (about 1 ml.). After this solution had been chilled (−20° C.), yellow crystals were collected by filtration, washed with ethanol, and dried in vacuo over P$_2$O$_5$ at 78° C. for 1.5 hours: yield, 66 mg. (33%); m.p., gradual decomposition; TLC, 1 spot (silica gel H, butanol-water-acetic acid (5:3:2), detection by UV and by potassium permanganate spray); IR (1700–1500 cm$^{-1}$ region) 1640 sh, 1605 s, 1530 w; UVmax 348 nm ($\epsilon$22,100), 264 ($\epsilon$7600), 225 sh, 207 ($\epsilon$24,700) at pH 1; 341 ($\epsilon$25,900), 264 ($\epsilon$7900), 231 ($\epsilon$17,800), 207 ($\epsilon$22,100) at pH 7; 318 ($\epsilon$20,700), 269 ($\epsilon$7500), 251 ($\epsilon$12,000), 222 ($\epsilon$16,700) at pH 13; MS (free base, direct-probe temperature, 390° C.), m/e 297 (M), 280 (M−OH), 266 (M−CH$_2$OH), 250 (M−OH−CH$_2$OH+H), 248 (M−H$_2$O−CH$_2$OH), 222 (M−75), 194 (P+C$_2$H$_4$), 168 (P+2H), 167 (P+H); $^1$H NMR (Me$_2$SO-d$_6$) $\delta$1.4–2.4 (m, CH$_2$ and CHCH$_2$OH), 3.4 (m, CH$_2$OH) 3.82 (m, —CHOH—CH—CH$_2$OH), 4.23 (m, —N—CH—CHOH), 4.5 (m, broad, —N—CH, OH, H$_2$O acidic H), 6.95 (NH$_2$), 8.53 (s, purine CH), 12.21 (m, NH).

Analysis. Calcd. for C$_{11}$H$_{15}$N$_5$O$_3$S·H$_2$SO$_4$: C, 33.41; H, 4.34; N, 17.71. Found: C, 33.42; H, 4.30; N, 17.58

EXAMPLE 6

(1α,2α,3β,5β)-3-(5,7-Diamino-3H-1,2,3-triazolo[4,5-d]pyrimidin-3-yl)-5-(hydroxymethyl)-1,2-cyclopentanediol (Formula III, X=NH$_2$)

The 2-amino-6-chloro-8-azapurine represented by Formula III with X=Cl (875 mg.) was treated with liquid ammonia (35 ml.) at 60° C. for 18 hours by the method described for the preparation of the compound of Example 2. The solid remaining from the evaporation of volatile components from the reaction mixture was triturated with hot water (25 ml.), and the mixture was cooled in an ice bath. The solid was collected by filtration and dried in vacuo over P$_2$O$_5$ at 78° C. during 2 hours; weight, 806 mg. The crude product was recrystallized from water and dried as before: recovery, 91%; m.p., 224°–226° C., shrinking at 198° C.; MS (direct-probe temperature, 160° C.), m/e 281 (M), 264 (M−OH), 250 (M−CH$_2$OH), 234 (M−OH−CH$_2$OH+H), 206 (M−75), 194, 178 (P+C$_2$H$_4$), 176, 152 (P+2H), 151 (P+H), 150 (P), 126, 110; IR (1700–1500 cm$^{-1}$ region) 1670, 1635 s, 1605 s, 1505 s; UVmax 286 nm ($\epsilon$7700), 256 ($\epsilon$9600), 214 ($\epsilon$25,500) at pH 1; 287 ($\epsilon$10,700), 258 ($\epsilon$5800), 223 ($\epsilon$26,000) at pH 7 and 13.

Analysis. Calcd. for C$_{10}$H$_{15}$N$_7$O$_3$·H$_2$O: C, 40.13; H, 5.73; N, 32.76. Found: C, 40.46; H, 5.64; N, 33.02.

Analytical data obtained from specimens dried for a longer period or at a higher temperature were in agreement with the composition of the desired product either unhydrated or as a one-fourth hydrate. Three melting temperatures were observed, the highest being 245°–247° C.; for example, a specimen dried at 78° C. for 2 hours and then at 100° C. for 4 hours melted at 199°–200° C., resolidified, melted again at 224°–226° C., resolidified, and melted with decomposition at 245°–247° C.

EXAMPLE 7

(1α,2α,3β,5β)-3-[5-Amino-7-(methylthio)-3H-1,2,3-triazolo-[4,5-d]pyrimidin-3-yl]-5-(hydroxymethyl)-1,2-cyclopentanediol (Formula III, X=—SCH$_3$)

Methanethiol was passed from a cylinder containing the compressed gas into a flask that was immersed in a dry ice-acetone bath at −70° C. and that contained a mixture of anhydrous magnesium sulfate and anhydrous calcium sulfate. The cold mixture was shaken for 3 hours to dry the liquid methanethiol (25–30 ml.), and the thiol was then passed as a gas into a mixture, protected from atmospheric moisture, of 286 mg. of the 2-amino-6-chloro-8-azapurine (Formula III with X=Cl) and 25 ml. of anhydrous methanol (dried over molecular sieves). A solution of sodium methoxide in methanol (1.48M, 1.35 ml.) was then added, and the mixture was stirred at room temperature under a dry ice condenser for 12 hours. The reaction mixture was concentrated to dryness, the residual solid was dissolved in a mixture of methanol (20 ml.) and water (3 ml.), the solution was neutralized (pH 6–7) with 2N hydrochloric acid and then concentrated, and the concentrated mixture containing a crystalline precipitate was stored at 5° C. overnight. The white crystalline solid was collected by filtration and dried in vacuo over P$_2$O$_5$ at room temperature: yield, 242 mg. (82%); m.p. 143°–146° C.; MS, m/e 312 (M). TLC revealed the presence of a small amount of an impurity, HPLC indicated that the ratio of the desired 5-amino-7-(methylthio)-3H-1,2,3-triazolo[4,5-d]pyrimidine to the impurity was 95:5, and a $^1$H NMR spectrum indicated that the impurity was the analogous 5-amino-7-methoxy derivative ($\delta$4.08, s, OCH$_3$). A specimen was purified further by preparative TLC on silica gel (86:14 butanol-water) and then by recrystallization from water: m.p. 149°–150° C. dec.; MS (direct-probe temperature, 20° C.), m/e 312 (M), 297 (M−CH$_3$), 295 (M−OH), 284 (M−N$_2$), 281 (M−OH), 265 (M−SCH$_3$, M−OH−CH$_2$OH+H), 237 (M−75), 235, 225, 209 (P+C$_2$H$_4$), 207, 183 (P+2H), 182 (P+H), 180 (P), 167, 165, 157, 155; IR (1700–1500 cm$^{-1}$ region) 1625, 1590 s, 1560 s, 1495 s; $^1$H NMR (Me$_2$SO-d$_6$) $\delta$1.6–2.5 (m, CH$_2$ and CH—CH$_2$OH), 2.67 (s, SCH$_3$), 3.32 (H$_2$O), 3.48 (m, CH$_2$OH), 3.88 (m, —CHOH—CH—CH$_2$OH), 4.36 (m, —N—CH—CHOH), 4.9 (m, —N—CH—), 4.6–5.1 (m, 3OH), 7.16 (NH$_2$); UVmax 313 nm ($\epsilon$10,800), 278 ($\epsilon$9400), 245 sh, 223 ($\epsilon$16,900) at pH 1; 318 ($\epsilon$10,400), 277 ($\epsilon$8500), 247 sh, 225 ($\epsilon$17,400) at pH 7; 317 ($\epsilon$10,700), 275 ($\epsilon$8600), 245 sh, 223 ($\epsilon$16,900) at pH 13.

Analysis. Calcd. for C$_{11}$H$_{16}$N$_6$O$_3$S.0.67H$_2$O: C, 40.73; H, 5.39; N, 25.91. Found: C, 40.95; H, 5.41; N, 25.96.

EXAMPLE 8

5-Amino-3,6-dihydro-3-[(1$\alpha$,2$\beta$,3$\beta$,4$\alpha$)-2,3-dihydroxy-4-(hydroxymethyl)cyclopentyl]-7H-1,2,3-triazolo[4,5-d]pyrimidine-7-thione (Formula IV, Y=S).

A solution prepared by adding 2.3 g. of sodium to 100 ml. of cold (5° C.) absolute ethanol was sparged with hydrogen sulfide at 5° C. for 1 hr. to form sodium hydrogen sulfide. The 2-amino-6-chloro-8-azapurine (Formula III with X=Cl; 300 mg., 1.0 millimole) was added to 10 ml. (10 millimoles) of the solution of sodium hydrogen sulfide, and the mixture was heated under reflux, under a dry-ice condenser, for 2 hrs. and then allowed to stand overnight. The reaction mixture was diluted with water (3 ml.), acidified to pH 4, and filtered to remove a solid. A mixture of the solid (278 mg.) and water (1 ml.) was boiled briefly, cooled to 5° C., and filtered to separate the solid; weight, 147 mg. The first filtrate was diluted with water (25 ml.), concentrated to about 10 ml., and filtered to collect a second crop of the crude product; weight, 107 mg. The total crude product (both crops combined) was recrystallized from water, and the yellow crystalline product was separated from the cold mixture by filtration and dried in vacuo over phosphorus pentoxide at 78° C. for 2 hrs.: yield, 165 mg. (53%); m.p., 149°–153° C., resolidified, remelted at 238°–240° C. dec.; UVmax 234, 254, 285, and 333 nm at pH 7; 253, 288, and 326 nm at pH 13.

Analysis. Calcd. for C$_{10}$H$_{14}$N$_6$O$_3$S.3/4H$_2$O: C, 38.51; H, 5.02; N, 26.96. Found: C, 38.46; H, 4.82; N, 27.19.

EXAMPLE 9

Antiviral Activity of Carbocyclic Analogs of 2-Amino-6-substituted-purine Ribofuranosides and of 2-Amino-6-substituted-8-azapurine Ribofuranosides Carbocyclic analogs (Formulas I–IV) of the ribofuranosides named in the title were tested for antiviral activity against viruses that replicate in mammalian cells growing in cell culture. The results of these tests against herpes simplex virus, type 1, and against vaccinia virus are summarized in Table 1. The Virus Rating (VR) is a weighted measurement of antiviral activity determined by the method of Ehrlich et al., *Annals of the New York Academy of Science*, Volume 130, pages 5–16, 1965. In tests carried out by this method, a VR of 0.5–0.9 indicates marginal to moderate antiviral activity, and a VR equal to or greater than 1 indicates definite antiviral activity. The higher the value of VR, the greater is the antiviral activity. The MIC$_{50}$ (minimum inhibitory concentration, 50%) is the concentration of a test compound required for 50% inhibition of virus-induced cytopathogenic effects. The tests summarized in Table 1 show that carbocyclic analogs of ribofuranosides of 2-amino-6-substituted-purines and of 2-amino-6-substituted-8-azapurines possess definite antiviral activity. Especially significant is the very high activity exhibited by the carbocyclic analog (Example 2; Formula I, X=NH$_2$) of 2,6-diaminopurine ribofuranoside. Virus ratings (VR) of 4.6, 2.2, and 3.8 were observed in tests vs. strain HFK of HSV-1, strain 377 of HSV-1, and vaccinia virus, respectively. The results summarized in Table 1 show that other ribofuranoside analogs possess significant and unequivocal activity against strain HF of HSV-1, strain 377 of HSV-1, or both strains.

TABLE 1

Antiviral Activity of Carbocyclic Analogs of Ribofuranosides of 2-Amino-6-substituted-purines and 2-Amino-6-substituted-8-azapurines[1]

| Compound | Herpes Simplex Type 1 | | | Vaccinia Virus | |
|---|---|---|---|---|---|
| | Strain | VR | MIC$_{50}$ mcg./ml. | VR | MIC$_{50}$ mcg./ml. |
| Example 1; Formula I, X = Cl | HF | 1.7 | 10 | 1.2 | 20 |
| Formula IV, Y = O | 377 | 2.2 | 58 | | |
| Example 2; Formula I, X = NH$_2$ | HF | 4.6 | 0.3 | 3.8 | 2.3 |
| | 377 | 2.2 | 197 | | |
| Example 3; Formula I, X = NHCH$_3$ | HF | 1.3 | 320 | | |
| Formula III, X = Cl | HF | 0.9 | 81 | 0.6 | |
| Example 6; Formula III, X = NH$_2$ | HF | 1.4 | 100 | | |
| | 377 | 0.6 | | | |
| Ara-A (positive control) | HF | 2.0–2.2 | 2.5–10 | | |

[1]Antiviral assays of these compounds were performed by using the HF strain of HSV-1 and the Lederle Chorioallantoic strain of vaccinia virus, both replicating in Human Epidermoid Carcinoma No. 2 (H.Ep.-2) cells, or strain 377 of HSV-1 replicating in Vero cells.

Although the invention has been described in considerable detail with specific reference to certain advantageous embodiments thereof, variations and modifications can be made without departing from the scope of the invention as described in the specification and defined in the appended claims.

We claim:

1. A compound having one of the following formulas:

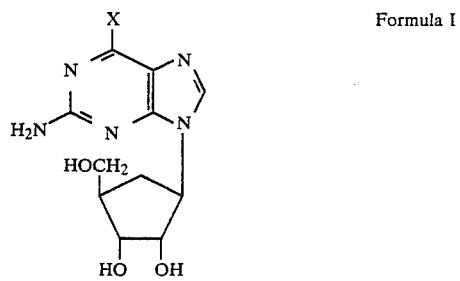

Formula I

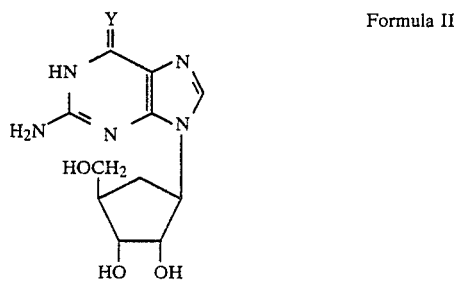

Formula II

-continued

Formula III

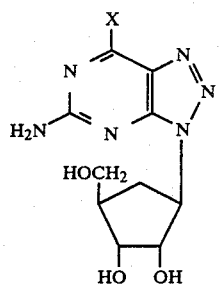

Formula IV

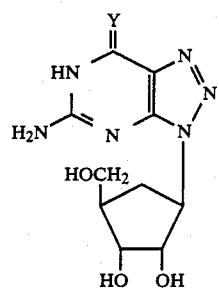

wherein X is fluorine, iodine, bromine, an amino group, an alkylamino group, an alkoxy group or an alkylthio group and Y is sulfur.

2. A compound as defined in claim 1 which is (1α,2α,3β,5β)-3-(2,6-diamino-9H-purin-9-yl)-5-(hydroxymethyl)-1,2-cyclopentanediol.

3. A compound as defined in claim 1 which is (1α,2α,3β,5β)-3-[2-amino-6-(methylamino)-9H-purin-9-yl]-5-(hydroxymethyl)-1,2-cyclopentanediol.

4. A compound as defined in claim 1 which is (1α,2α,3β,5β)-3-[2-amino-6-(methylthio)-9H-purin-9-yl]-5-(hydroxymethyl)-1,2-cyclopentanediol.

5. A compound as defined in claim 1 which is 2-amino-1,9-dihydro-9-[(1α,2β,3β,4α)-2,3-dihydroxy-4-(hydroxymethyl)cyclopentyl]-6H-purine-6-thione.

6. A compound as defined in claim 1 which is (1α,2α,3β,5β)-3-(5,7-diamino-3H-1,2,3-triazolo[4,5-d]pyrimidin-3-yl)-5-(hydroxymethyl)-1,2-cyclopentanediol.

7. A compound as defined in claim 1 which is (1α,2α,3β,5β)-3-[5-amino-7-(methylthio)-3H-1,2,3-triazolo[4,5-d]pyrimidin-3-yl]-5-(hydroxymethyl)-1,2-cyclopentanediol.

8. A compound as defined in claim 1 which is 5-amino-3,6-dihydro-3-[(1α,2β,3β,4α)-2,3-dihydroxy-4-(hydroxymethyl)-cyclopentyl]-7H-1,2,3-triazolo[4,5-d]pyrimidine-7-thione.

* * * * *